(12) United States Patent
Banning et al.

(10) Patent No.: US 9,394,319 B2
(45) Date of Patent: Jul. 19, 2016

(54) BORON SUBPHTHALOCYANINE COMPOUNDS AND METHOD OF MAKING

(71) Applicant: XEROX CORPORATION, Norwalk, CT (US)

(72) Inventors: Jeffrey H. Banning, Hillsboro, OR (US); Wolfgang G. Wedler, Tualatin, OR (US); Stephan V. Drappel, Toronto (CA)

(73) Assignee: XEROX CORPORATION, Norwalk, CT (US)

( * ) Notice: Subject to any disclaimer, the term of this patent is extended or adjusted under 35 U.S.C. 154(b) by 326 days.

(21) Appl. No.: 14/012,132

(22) Filed: Aug. 28, 2013

(65) Prior Publication Data

US 2015/0065729 A1    Mar. 5, 2015

(51) Int. Cl.
*C09B 47/30* (2006.01)
*C07F 5/02* (2006.01)

(52) U.S. Cl.
CPC ............. *C07F 5/022* (2013.01); *C09B 47/30* (2013.01)

(58) Field of Classification Search
CPC .............................. C07F 5/022; C09B 47/30
See application file for complete search history.

(56) References Cited

U.S. PATENT DOCUMENTS

| | | |
|---|---|---|
| 4,490,731 A | 12/1984 | Vaught |
| 5,782,966 A | 7/1998 | Bui et al. |
| 6,174,937 B1 | 1/2001 | Banning et al. |
| 6,309,453 B1 | 10/2001 | Banning et al. |
| 6,368,395 B1 | 4/2002 | Nohr et al. |
| 6,472,523 B1 | 10/2002 | Banning et al. |
| 6,476,219 B1 | 11/2002 | Duff et al. |
| 6,998,493 B2 | 2/2006 | Banning et al. |
| 7,030,176 B2 | 4/2006 | Nohr et al. |
| 8,057,589 B2 | 11/2011 | Banning |
| 8,920,551 B1 * | 12/2014 | Banning ............... C09D 11/328 106/31.29 |
| 8,981,088 B1 * | 3/2015 | Banning ................. C09B 47/30 544/184 |

FOREIGN PATENT DOCUMENTS

ES            2116867 A1  *  7/1998

OTHER PUBLICATIONS

Gonzalez-Rodriguez et al. "Photoinduced Charge-Transfer States in Subphthalocyanine—Ferrocene Dyads" Journal of the American Chemical Society, 2006, vol. 128, pp. 10680-10681 and Supporting Information pp. S1-S28.*
Brisson et al. "Boron Subphthalocyanine Dyes: 3-Pentadecylphenol as a Solubilizing Molecular Fragment" Industrial & Engineering Chemistry Research, 2011, vol. 50, pp. 10910-10917.*
McMurry, John "Organic Chemistry: Fourth Edition", Brooks/Cole, 1996, p. 694.*
Banning et al., "Phase Change Inks", U.S. Appl. No. 14/011,766, filed Aug. 28, 2013.
Banning et al., "Boron Subphthalocyanine Compounds and Method of Making", U.S. Appl. No. 14/012,222, filed Aug. 28, 2013.
Wikipedia, Phthalonitrile, http://en.wikipedia.org/wiki/Phthalonitrile, retrieved Mar. 25, 2013, pp. 1-3.
Wikipedia, Phthalocyanine, http://en.wikipedia.org/wiki/Phthalocyanine, retrieved Mar. 25, 2013, pp. 1-4.
Unknown Author, Substructure Search Results, http://sigmaaldrich.com/catalog/search/substructure/SubstructureSearchPate, retrieved May 10, 2013, 4 pages.
Brisson et al., "Boron Subphthalocyanine Dyes: 3-Pentadecylphenol as a Solubilizing Molecular Fragment", Ind. Eng. Chem. Res., 50, 2011, pp. 10910-10917.

* cited by examiner

*Primary Examiner* — Joseph Kosack
(74) *Attorney, Agent, or Firm* — MH2 Technology Law Group LLP

(57) ABSTRACT

A compound comprising a boron subphthalocyanine moiety, a plurality of solubilizing substituents positioned on peripheral cyclic groups of the boron subphthalocyanine moiety and an axial substituent positioned on the boron atom of the boron subphthalocyanine moiety. The plurality of solubilizing substituents comprise an oxygen or sulfur containing functional group and a substituted or unsubstituted, linear, branched or cyclic, aliphatic or aromatic terminal hydrocarbyl group that is 8 or more carbon atoms in length, the hydrocarbyl group optionally containing one or more heteroatoms. The axial substituent is selected from the group consisting of halogen, alkyloxy, haloalkyloxy, ester, carbonyl substituted alkyl, carbonyl substituted haloalkyl, alkylaryloxy, haloalkylaryloxy, alkyl sulfonyl, haloalkyl sulfonyl, alkylaryl sulfonyl and haloalkylaryl sulfonyl. The compound is not one of the following compounds: a) Phenoxytrispentadecylphenoxyboronsubphthalocyanine, b) Chlorotrispentadecylphenoxyboronsubphthalocyanine, or c) 3-Pentadecylphenoxytrispentadecylphenoxyboronsubphthalocyanine. Processes for making the compound are also taught.

6 Claims, No Drawings

BORON SUBPHTHALOCYANINE COMPOUNDS AND METHOD OF MAKING

FIELD OF THE DISCLOSURE

The present disclosure is directed to boron subphthalocyanine compounds and methods of making the compounds.

BACKGROUND

Ink jet printing processes may employ inks that are solid at room temperature and liquid at elevated temperatures. Such inks may be referred to as solid inks, hot melt inks, phase change inks and the like. For example, U.S. Pat. No. 4,490,731, the disclosure of which is incorporated herein by reference in its entirety, discloses an apparatus for dispensing phase change ink for printing on a recording medium such as paper.

In general, hot melt phase change inks are in the solid phase at ambient temperature, but exist in the liquid phase at the elevated operating temperature of an ink jet printing device. At the jetting temperature, droplets of liquid ink are ejected from the printing device and, when the ink droplets contact the surface of the recording medium, either directly or via an intermediate heated transfer belt or drum, they quickly solidify to form a predetermined pattern of solidified ink drops.

Phase change inks for color printing typically comprise a phase change ink carrier composition which is combined with a phase change ink compatible colorant. Because hot-melt solid inks printers often operate at printhead temperatures of 135° C. and higher, they often employ thermally stable and wax-soluble colorants that can withstand these relatively high operating temperatures. Examples of such colorants are the Phthalocyanine dyes disclosed in U.S. Pat. No. 6,472,523, the disclosure of which is hereby incorporated by reference in its entirety. These colorants are high-chroma phthalocyanine chromophore structures that are known for use as cyan dyes suitable for use in hot melt ink compositions. The Phthalocyanine dyes include waxy substituents that increase dye solubility in a waxy ink environment.

True "vibrant" magenta dyes are difficult to come by and hot melt ink soluble and stable versions are even more difficult to obtain. Most commercially available magenta dyes do not meet the performance requirements for solid ink. One example of a magenta dye that is known for use in solid inks is a wax soluble Rhodamine dye that is disclosed in U.S. Pat. No. 6,998,493, the disclosur e of which is hereby incorporated by reference in its entirety. Due primarily to the "economy of scale," this dye is quite expensive because it is custom manufactured. Additionally, the dye suffers problems with diffusion through the ink matrix, easily bleeding into other colored areas in prints within several days.

The process for synthesis of generic phenoxy substituted Copper phthalocyanines and Boron subphthalocyanines is also well known in the chemical arts. Such dyes generally are not very soluble in current hot melt ink platforms and hence cannot be used. Lack of solubility of dyes is generally known to cause problems in ink formulations, such aggregation of the dye and/or blooming.

The magenta dye known in the dye industry as Boron subphthalocyanine chloride has been more of an academic curiosity because of difficulty in preparation and for solubility reasons. See the compound of formula 1 below.

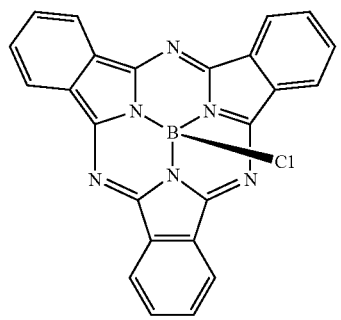

Boron Subphthalocyanine Chloride
CAS [36530-06-0]

(1)

New magenta dye compounds and processes for making such compounds that address one or more of the problems of known magenta dyes and/or provide magenta dye alternatives would be considered a step forward in the art. In addition, the ability to manufacture multiple custom-made dyes, such as both Cyan and Magenta dyes, using the same chemical intermediate compounds, could potentially provide a significant cost reduction.

SUMMARY

The present disclosure is directed to novel magenta dye compounds, and processes for making such compounds, which provide one or more of the following advantages: solubility in hot melt ink compositions, solubility in wax-based compositions, sufficient thermal stability for use at relatively high printhead temperatures, the ability to be employed in relatively low energy systems and/or in low printhead temperature systems, the ability to be used in UV cure systems, good lightfastness, minimal tendencies for dye diffusion, reduced cost for production, the ability to be modified in several dimensions in order to address physical property shortcomings and/or allow the dye compound to be tailored for differing applications, or the ability to be manufactured using known intermediate compounds.

An embodiment of the present disclosure is directed to a compound comprising a boron subphthalocyanine moiety, a plurality of solubilizing substituents positioned on peripheral cyclic groups of the boron subphthalocyanine moiety and an axial substituent positioned on the boron atom of the boron subphthalocyanine moiety. The plurality of solubilizing substituents comprise an oxygen or sulfur containing functional group and a substituted or unsubstituted, linear, branched or cyclic, aliphatic or aromatic terminal hydrocarbyl group that is 8 or more carbon atoms in length, the hydrocarbyl group optionally containing one or more heteroatoms. The axial substituent is selected from the group consisting of halogen, alkyloxy, aryloxy, arylalkyloxy, haloalkyloxy, ester, carbonyl substituted alkyl, carbonyl substituted haloalkyl, alkylaryloxy, haloalkylaryloxy, alkyl sulfonyl, haloalkyl sulfonyl, alkylaryl sulfonyl and haloalkylaryl sulfonyl. The compound is not one of the following compounds: a) Phenoxytrispentadecylphenoxyboronsubphthalocyanine, b) Chlorotrispentadecylphenoxyboronsubphthalocyanine, or c) 3-Pentadecylphenoxytrispentadecylphenoxyboronsubphthalocyanine.

An embodiment of the present disclosure is directed to a process for making a colorant compound. The processing comprises reacting a phthalonitrile compound with a boron halide salt to form a boron subphthalocyanine chloride intermediate. The phthalonitrile compound includes an oxygen or sulfur containing functional group substituted with a substituted or unsubstituted, linear, branched or cyclic, aliphatic or aromatic terminal hydrocarbyl group that is 8 or more carbon atoms in length, the hydrocarbyl group optionally containing one or more heteroatoms. The boron subphthalocyanine chloride intermediate is reacted with at least one oxygen containing compound selected from the group consisting of alcohols, carboxylic acids and sulfonic acids to form a colorant compound that provides a magenta color.

Yet another embodiment of the present disclosure is directed to a compound. The compound is made by the process comprising: reacting a phthalonitrile compound with a boron halide salt to form a boron subphthalocyanine chloride intermediate, the phthalonitrile compound including an oxygen or sulfur containing functional group substituted with a substituted or unsubstituted, linear, branched or cyclic, aliphatic or aromatic terminal hydrocarbyl group that is 8 or more carbon atoms in length, the hydrocarbyl group optionally containing one or more heteroatoms; and reacting the boron subphthalocyanine chloride intermediate with at least one oxygen containing compound selected from the group consisting of alcohols, carboxylic acids and sulfonic acids to form a colorant compound that provides a magenta color. The compound has L*a*b* color space values of: an a* value ranging from about 35 to about 53; a b* value of from about 24 to about 40; and a L* value of from about 40 to about 60. The compound is not one of the following compounds: a) Phenoxytrispentadecylphenoxyboronsubphthalocyanine, b) Chlorotrispentadecylphenoxyboronsubphthalocyanine, or c) 3-Pentadecylphenoxytrispentade-cylphenoxyboronsubphthalocyanine.

It is to be understood that both the foregoing general description and the following detailed description are exemplary and explanatory only and are not restrictive of the present teachings, as claimed.

DESCRIPTION OF THE EMBODIMENTS

Reference will now be made in detail to embodiments of the present teachings, examples of which are illustrated in the accompanying drawings. In the drawings, like reference numerals have been used throughout to designate identical elements. In the following description, reference is made to the accompanying drawing that forms a part thereof, and in which is shown by way of illustration a specific exemplary embodiment in which the present teachings may be practiced. The following description is, therefore, merely exemplary.

Wax Soluble Subphthalocyanine Compounds

An embodiment of the present disclosure is directed to a magenta colorant compound and intermediate compounds for forming the magenta colorant compound. The colorant compound is a substituted boron subphthalocyanine compound comprising a plurality of solubilizing substituents attached to peripheral cyclic groups of a boron subphthalocyanine moiety. An axial substituent is also attached to the boron atom in the subphthalocyanine moiety.

The solubilizing substituents comprise an oxygen or sulfur containing functional group attached to a terminal aromatic or aliphatic hydrocarbyl group that includes 8 or more carbon atoms. The hydrocarbyl group can be substituted or unsubstituted, linear branched or cyclic, and can include one or more hetero atoms, such as oxygen, nitrogen or sulfur. Examples of suitable hydrocarbyl groups include alkyl, arylalkyl, alkylaryl and aryl groups.

The number of carbon atoms in the hydrocarbyl groups can be varied so as to result in the solubility of the colorant compound in a desired wax-based composition, such as, for example, a phase change ink composition. In an embodiment, the terminal hydrocarbyls are linear or branched $C_{10}$ to $C_{50}$ alkyls, such as a $C_{12}$ to $C_{20}$ or $C_{25}$ alkyls. In an embodiment, the alkyl groups are linear alkyls of about 15 carbon atoms in length.

The oxygen or sulfur containing functional group to which the alkyl group of the solubilizing substituents is attached can be any suitable group that has sufficient reactivity to form the desired phthalonitrile intermediates. Examples of suitable functional groups include aryloxy, sulfoxy, sulfur, oxygen or sulfonyl groups.

The axial substituent for the magenta colorants of the present disclosure is positioned on the boron atom and can be any suitable oxygen containing group. Axial substituents can act to further enhance the solubility of the dye in the ink base and/or act as a stabilizing agent to, for example, stabilize the dye towards thermal degredation and/or towards lightfastness. Examples of suitable axial substituents include alkoxy, such as methoxy, ethoxy or propoxy; aryloxy, arylalkyloxy, haloalkyloxy, such as fluorinated or perfluorinated methoxy, ethoxy or propoxy; esters, such as acetyl or trifluoroacetyl; carbonyl substituted alkyls; carbonyl substituted haloalkyls; alkylaryloxy; haloalkylaryloxy; alkyl sulfonyls, such as methane sulfonyl; haloalkyl sulfonyls, such as trifluoromethane sulfonyl; alkylaryl sulfonyls, such as dodecylbenzene sulfonyl; and haloalkylaryl sulfonyls.

Intermediate compounds of the present disclosure can be similar to the magenta colorant compounds described above, but include a different axial substituent group attached to the boron atom. Examples of suitable axial substituent groups for the intermediate compounds can include halogens, such as chloro and bromo groups. The intermediate compounds can generally have similar solubility properties as the magenta compounds of the present disclosure, but may in some cases be a different color, such as violet or some other color.

In an embodiment, the colorant compound is a compound of formula I:

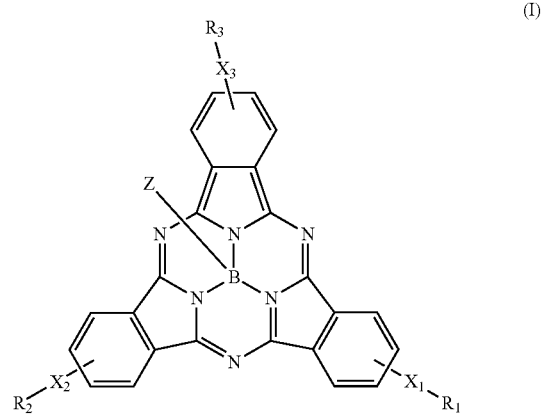

(I)

wherein:
$X_1$, $X_2$, and $X_3$ each, independently of the others, is —O—, —S—, —SO—, or —SO$_2$—;
$R_1$, $R_2$, and $R_3$ each, independently of the others, is:
  (1) alkyl, including substituted and unsubstituted alkyl, wherein hetero atoms may optionally be present in the alkyl;
  (2) aryl, including substituted and unsubstituted aryl, wherein hetero atoms may optionally be present in the aryl;

(3) arylalkyl, including substituted and unsubstituted arylalkyl, wherein hetero atoms may optionally be present in either the aryl or the alkyl portion of arylalkyl; or (4) alkylaryl, including substituted and unsubstituted alkylaryl, wherein hetero atoms may optionally be present in either the aryl or the alkyl portion of alkylaryl; and Z is:
(1) —$OR_4$, wherein $R_4$ is:
  (A) alkyl, including substituted and unsubstituted alkyl, wherein hetero atoms may optionally be present in the alkyl;
  (B) aryl, including substituted and unsubstituted aryl, wherein hetero atoms may optionally be present in the aryl;
  (C) arylalkyl, including substituted and unsubstituted arylalkyl, wherein hetero atoms may optionally be present in either the aryl or the alkyl portion of the arylalkyl; or
  (D) alkylaryl, including substituted and unsubstituted alkylaryl, wherein hetero atoms may optionally be present in either the aryl or the alkyl portion of the alkylaryl;

(2)

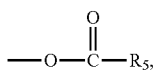

wherein $R_5$ is: alkyl, including substituted and unsubstituted alkyl, wherein hetero atoms may optionally be present in alkyl; or (3)

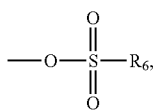

wherein $R_6$ is: alkyl, including substituted and unsubstituted alkyl, wherein hetero atoms may optionally be present in alkyl; and with the proviso that if Z is halogen, then $X_1$, $X_2$, and $X_3$ each, independently of the others, is selected from the group consisting of —S—, —SO—, and —$SO_2$—.

In an embodiment, the —$X_1$—$R_1$, —$X_2$—$R_2$, and —$X_3$—$R_3$ groups are selected from the group consisting of:

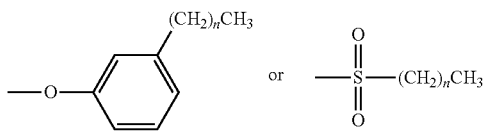

wherein n is an integer ranging from about 8 to about 50.

In an embodiment, the Z group of the compounds of formula I are selected from the group consisting of:

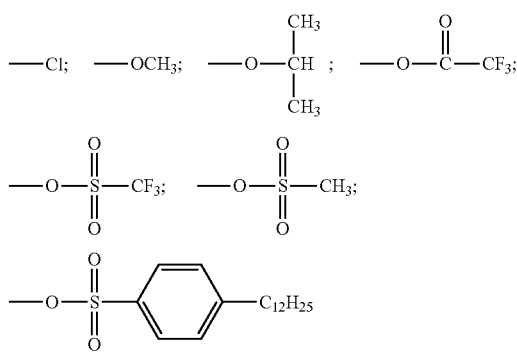

Specific examples of the colorant compounds of the present disclosure include the following:

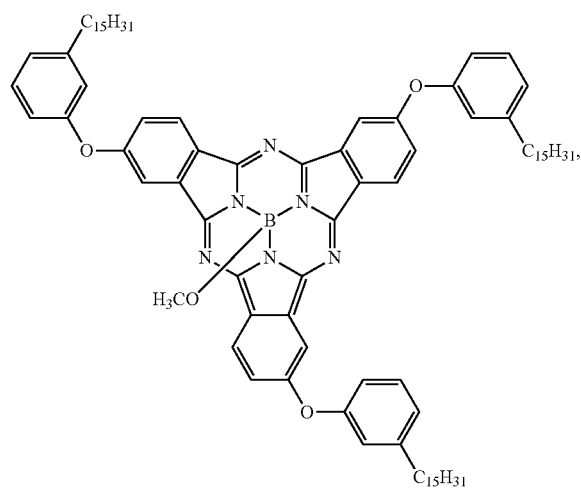

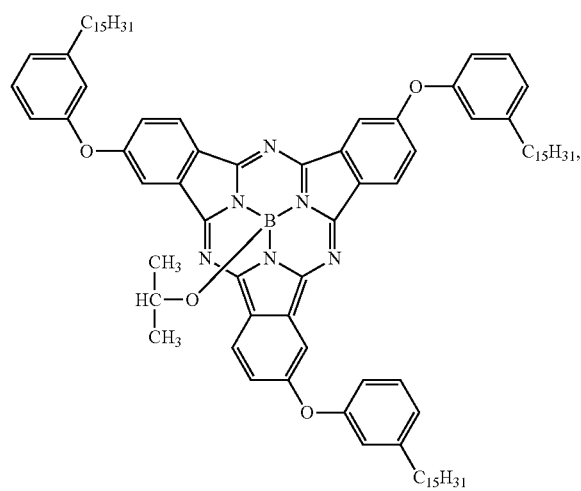

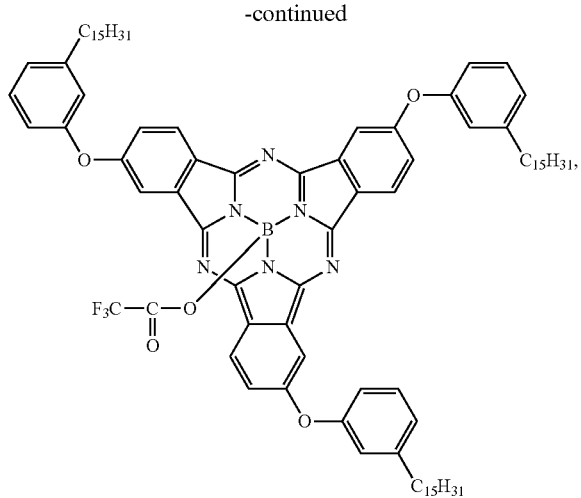

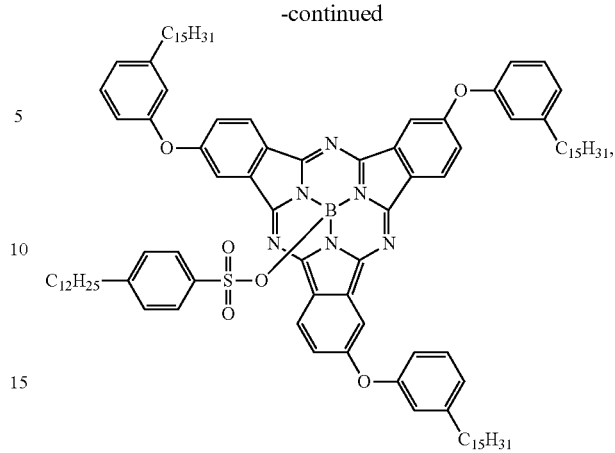

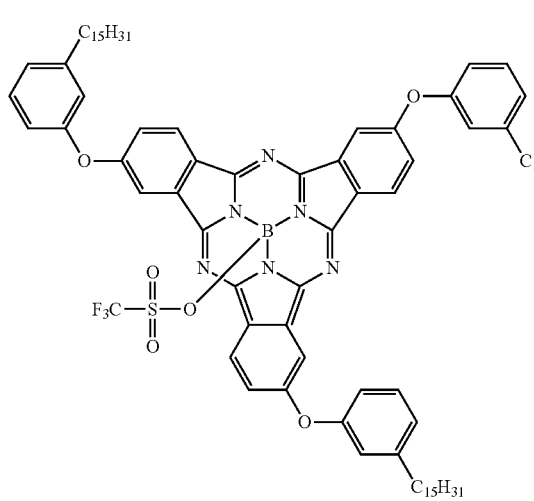

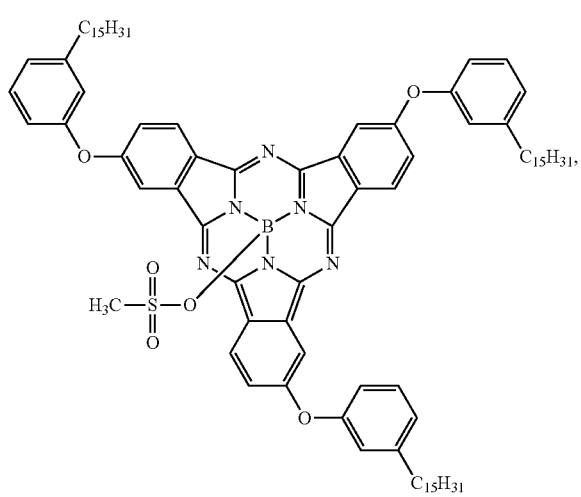

The L*a*b* color space is a well known color system that defines color using L* for lightness and a* and b* for color-opponent dimensions. In an embodiment, the colorant compounds of the present disclosure have the following L*a*b* color space values: a L* value ranging from about 40 to about 60, such as about 43 to about 57, or about 45 to about 55; an a* value ranging from about 35 to about 53, such as about 38 to about 50, or about 40 to about 48; and a b* value ranging from about −24 to about −40, such as about −26 to about −38, or about −28 to about −36. In addition, the colorant compounds can have a c* value ranging from about 49 to about 60, where c* is a measure of chromaticity.

The intermediate compounds of the present disclosure can be similar to those of formula I discussed above, except that Z is a halogen. An example of such an intermediate compound is shown below:

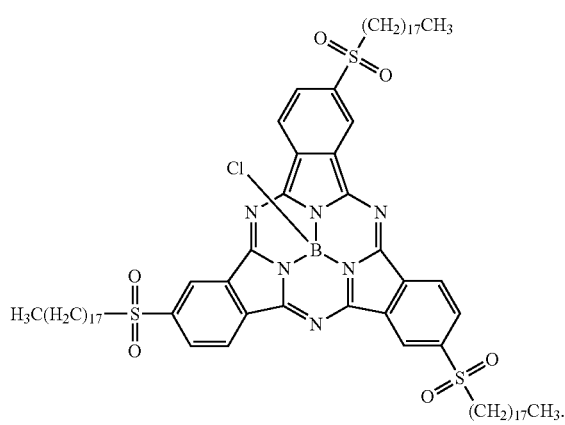

In an embodiment, the compounds of the present disclosure do not include the following: a) Phenoxytrispentadecylphenoxyboronsubphthalocyanine, b) Chlorotrispentadecylphenoxyboronsubphthalocyanine, or c) 3-Pentadecylphenoxytrispentadecylphenoxyboronsubphthalocyanine.

Process of Making the Compounds

The present disclosure is also directed to processes for making a colorant compound. In an embodiment, the process comprises reacting a phthalonitrile compound with a boron halide salt. The resulting subphthalocyanine intermediate can be, for example, any of the intermediate compounds described above. The intermediate compound is then reacted with at least one oxygen containing compound, such as compounds selected from the group consisting of alcohols, carboxylic acids and sulfonic acids, to form a colorant compound that provides a magenta color.

The phthalonitrile compounds employed in the process can include an oxygen or sulfur containing functional group substituted with a terminal aromatic or aliphatic hydrocarbyl having at least 8 carbon atoms. The hydrocarbyl group can be substituted or unsubstituted, linear, branched or cyclic, and can include one or more hetero atoms, such as oxygen, nitrogen or sulfur. Examples of suitable hydrocarbyl groups include alkyl, arylalkyl, alkylaryl and aryl groups.

In an embodiment, the phthalonitrile compounds are selected from the group consisting of $C_{10}$ to $C_{50}$ alkyl phenoxy substituted phthalonitriles and $C_{10}$ to $C_{50}$ alkyl sulfone substituted phthalonitriles, or mixtures thereof. Other long chain alkyl substituted phthalonitrile compounds can also be employed. One example of a commercially available phthalonitrile compound that can be used to make the colorant compounds of the present disclosure is 4-(3-pentadecylphenoxy)-phthalonitrile, which is disclosed in U.S. Pat. No. 6,472,523, issued to Jeffrey H. Banning et al.

Alkyl sulfone substituted phthalonitrile compounds employed in the processes of the present disclosure can be made by any suitable method. In an embodiment, the sulfur atom in an alkylsulfide-phthalonitrile compound is oxidized to form a sulfonyl functional group. This can be accomplished in any desired manner, such as by dissolving an alkylsulfide-phthalonitrile precursor in one or more solvents, such as methylisobutylketone and/or glacial acetic acid; followed by reaction of the sulfide group with a strong oxidizer, such as hydrogen peroxide.

Any suitable boron halide salt can be employed. In an embodiment, the boron halide salt is boron trichloride or boron tribromide.

The phthalonitrile compound and the boron halide salt can be reacted in any suitable manner to form the desired boron subphthalocyanine chloride intermediate. In an embodiment, phthalonitrile compounds are mixed with a non-aqueous solvent, such as xylenes or toluene. All or substantially all water can then be removed from the mixture by any suitable method, such as heating under an inert gas atmosphere, such as nitrogen or with a Dean Stark trap. The resulting mixture can then be combined with boron halide salt, which is optionally dissolved in a non-aqueous solvent, to form the boron subphthalocyanine chloride intermediate.

The boron subphthalocyanine chloride intermediate can then be mixed with a suitable oxygen containing compound, which reacts to replace the halogen atom as the axial substituent attached to the boron atom. Examples of suitable oxygen containing compounds include alcohols, phenols, carboxylic acids and sulfonic acids.

Examples of suitable alcohols for use as the oxygen containing compound in the processes of the present disclosure include compounds of formula:

$R_4OH$, wherein $R_4$ is selected from the group consisting of: substituted or unsubstituted alkyls optionally containing one or more hetero atoms; substituted or unsubstituted aryls optionally containing one or more hetero atoms; substituted or unsubstituted arylalkyls optionally containing one or more hetero atoms; and substituted or unsubstituted alkylaryls optionally containing one or more hetero atoms. Specific examples include methanol, ethanol and isopropyl alcohol.

Examples of suitable carboxylic acids include those having a formula:

$R_5COOH$ wherein $R_5$ is a substituted or unsubstituted alkyl optionally containing one or more hetero atoms. Specific examples include acetic acid, propanoic acid, trifluoroacetic acid and perfluorinated propanoic acid.

Examples of suitable sulfonic acids include those having a formula:

$R_6SO_3H$ wherein $R_6$ is a substituted or unsubstituted alkyl optionally containing one or more hetero atoms. Specific examples include trifluoromethane sulfonic acid, methane sulfonic acid and dodecylbenzene sulfonic acid.

EXAMPLES

These following examples are intended to be illustrative only, and the claims are not limited thereby. All parts and percentages are by weight unless otherwise indicated.

Example 1A

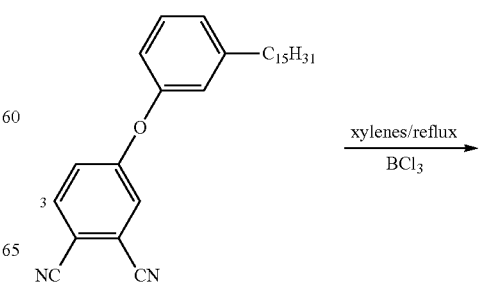

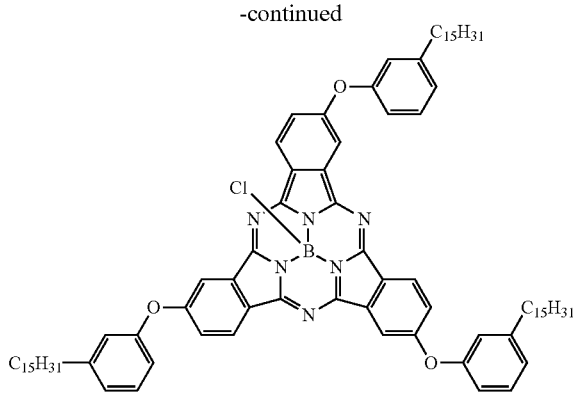

To a 500 mL three-necked, roundbottom flask equipped with Dean-Stark trap, condenser, and TEFLON coated stir magnet was charged 50.0 g 4-(3-pentadecylphenoxy)-phthalonitrile compound, prepared as described in Example I of U.S. Pat. No. 6,472,523, the disclosure of which is incorporated herein by reference in its entirety, and 300 mL xylenes. The flask was placed in a 160° C. oil bath under magnetic stirring, condenser, Dean-Stark apparatus, and light nitrogen blanket. After refluxing for 20 hours to remove all water, 42 mL of 1.0M boron trichloride in xylenes (about 4.5 g of actual $BCl_3$) were added under dry conditions via syringe and septum. The solution turned a violet color. The product was believed to be of the formula shown below and to the left.

Example 1B

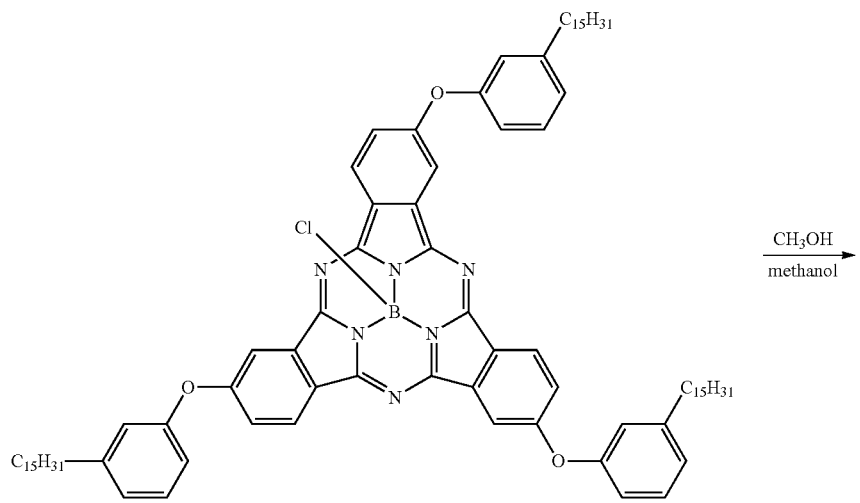

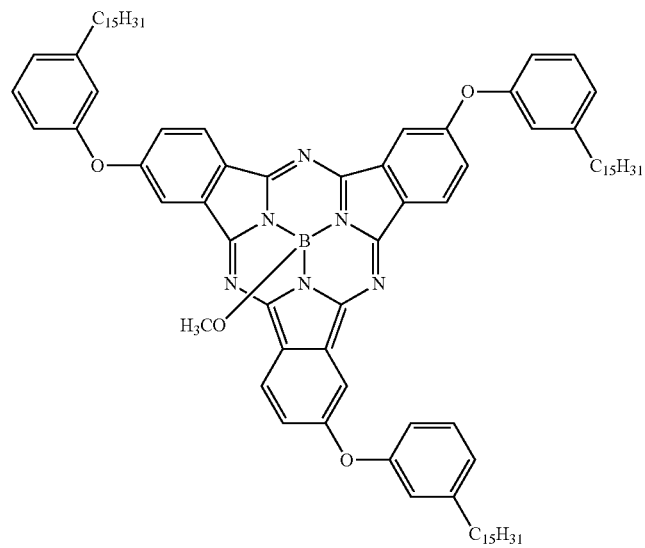

One hour after the addition reaction described in Example 1A, the solution was quenched into 1 L methanol and allowed to cool and set overnight. The methanol solution was then decanted leaving an oily solid which was collected with toluene. A strong magenta color was apparent in the toluene solution. If the solid product was allowed to remain dry overnight the color died. If the solid was dissolved in toluene or hexanes before being able to dry, a beautiful magenta color remained indefinitely. The structure was believed to be that shown above and to the right.

Example 2A

To a 500 mL three-necked, roundbottom flask equipped with Dean-Stark trap, condenser, and TEFLON coated stir magnet was charged 8.75 g 4-(3-pentadecylphenoxy)-phthalonitrile compound, prepared as described in Example I of U.S. Pat. No. 6,472,523, and 200 mL xylenes. The flask was placed in a 160° C. oil bath under magnetic stirring, condenser, Dean-Stark apparatus and light nitrogen blanket. After refluxing for 20 hours to remove all water, 20 mL of 1.0 M boron trichloride in xylenes were added under dry conditions via syringe and septum. The solution turned a violet color.

Example 2B

One hour after the addition reaction of Example 2B, the solution was quenched into 700 mL isopropanol and allowed to cool and set overnight. The isopropanol solution was then decanted leaving an oily solid. The structure is believe to be that shown below:

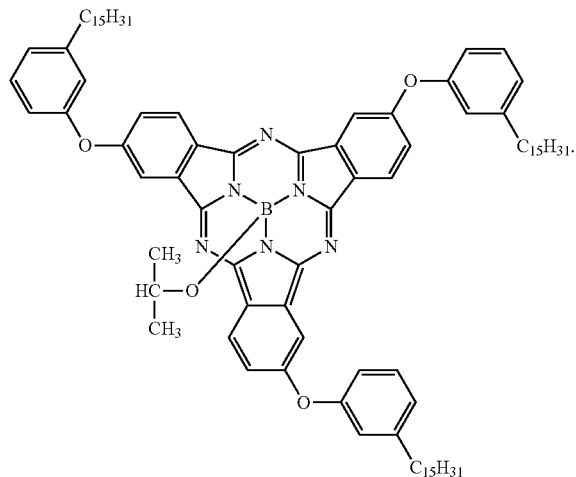

Example 3

The process of Example 1A was repeated. One hour after the addition reaction as described in Example 1A, the solution was quenched into 1 L methanol with 5 g trifluoroacetic acid, stirred for 20 min, stopped stirring, and allowed to cool and set overnight. The methanol solution was then decanted leaving an oily solid which was collected with toluene. A strong magenta color was apparent in toluene solution. The structure was believed to be that below:

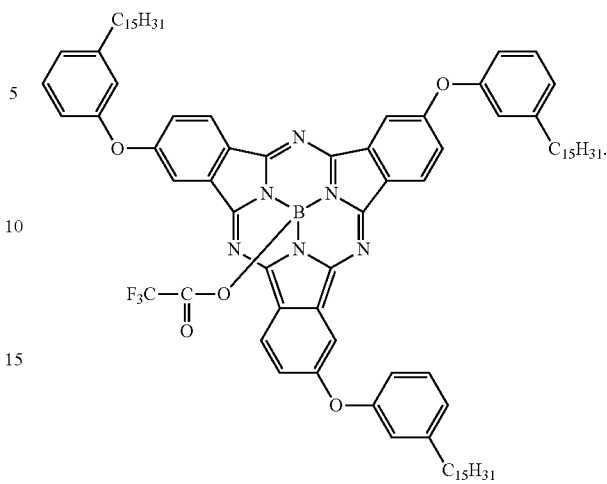

Example 4

The process of Example 1A was repeated. Refluxing was continued, and 1 h after the addition reaction as described in Example 1A, the solution was quenched equally (i.e., one third into each of three beakers) into three 1 L beakers containing:

A) 500 mL methanol with 1.9 g trifluoromethanesulfonic acid

B) 500 mL methanol with 1.2 g methanesulfonic acid

C) 500 mL methanol with 4.1 g dodecylbenzene sulfonic acid.

Each of solutions A, B and C were stirred for 20 min, stopped stirring and allowed to cool and set overnight. The methanol solution was then decanted leaving an oily solid. The oily solids were washed with a subsequent 300 mL methanol and decanted leaving deep red solids which were collected with methylene chloride and transferred to jars allowing the methylene chloride to evaporate. Strong magenta colors were apparent when the solids were taken up in toluene solution. The solids were stable indefinitely in air without loss of color. The structures were believed to be those shown below:

A)

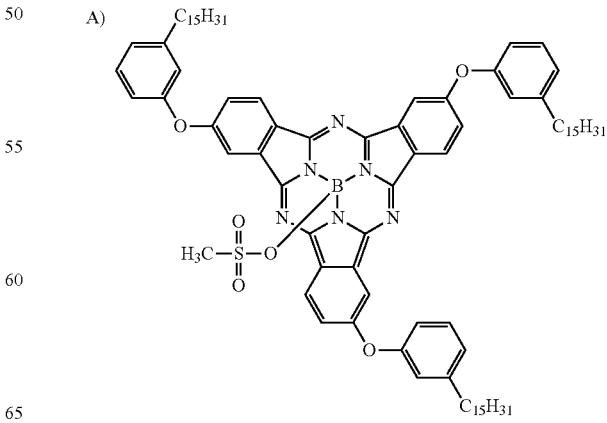

-continued

B) 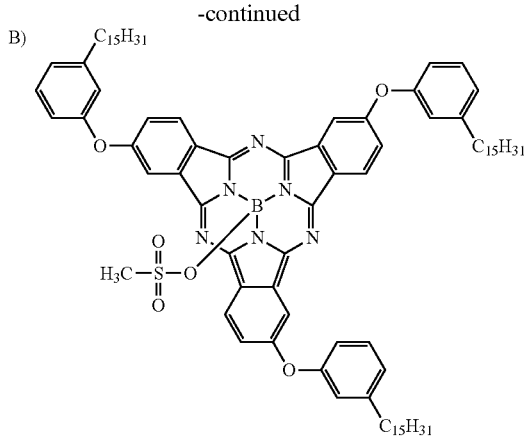

C) 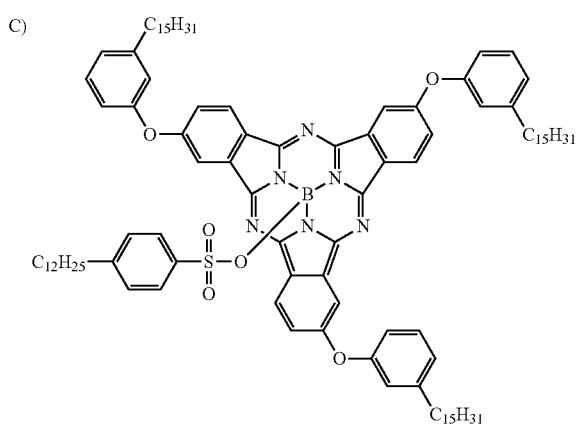

Example 5

To a 500 mL one-necked, roundbottom flask, condenser, and TEFLON coated stir magnet was charged 40.0 g 4-(3-pentadecylphenoxy)-phthalonitrile compound, prepared as described in Example I of U.S. Pat. No. 6,472,523, and 230 mL xylenes. The contents of the flask were stirred at room temperature until everything dissolved. An ice bath was then employed to cool the reaction mixture to 0° C. Thereafter, 33.3 mL BCl₃ in xylene was added over 30 min through the top of the condenser. The reaction mixture was then stirred for 10 min at 25° C. and placed in a 60° C. oil bath. The temperature of the oil bath was increased to 160° C. and a deep red/purple color began to develop. The reaction mixture was allowed to heat/stir/reflux for 6 hours. The purple/magenta reaction mixture was then quenched into 1 L acetone containing 5 g trifluoroacetic acid, stirred for 1 hour, covered with a watch-glass, and allowed to cool and settle for 2 days. Thereafter, 1 L methanol was added and the mixture was allowed to settle 2 days, after which the solvent was decanted off. A deep magenta oil was left. Trituration and decantation with 300 mL methanol twice yielded a deep magenta waxy solid which was collected with methylene chloride. A strong magenta color was apparent in toluene solution. The solid was stable indefinitely in air without loss of color.

Example 6A

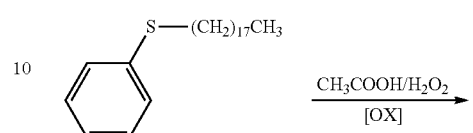

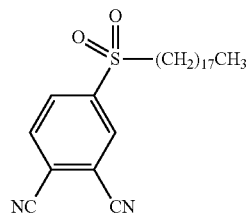

To a 24/40 2 L 3-neck flask with TELFON coated stir magnet, condenser, glass stopper, and constant pressure addition funnel in a silicone oil bath was added 25 g 4-octadecyl-sulfide-phthalonitirile, 137 g methylisobutylketone, and 127 g glacial acetic acid and began stirring. The temperature of the bath was increased from 25° C. to 90° C. and the solids were allowed to dissolve. 125 mL 35% H₂O₂ was added to the addition funnel and slowly added over 2 hours while the reaction mixture was stirred at 90° C. and then post heated at 90° C. for 1 hour. Stirring was then stopped and the mixture was allowed to come to 25° C. and set for 16 hours. A white solid cake formed on top of the contents of the flask. The liquid was decanted off and the solids were collected in a Buchner funnel and washed with methanol until no odor was detected. The solid was allowed to dry and thin layer chromatography ("TLC") was employed to show the disappearance of the starting S-reactant and the appearance of the final SO₂ product. An infrared spectrum was run on the product. The structure was believed to be that shown above.

Example 6B

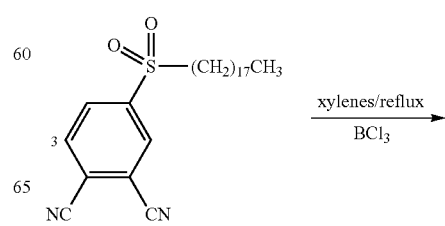

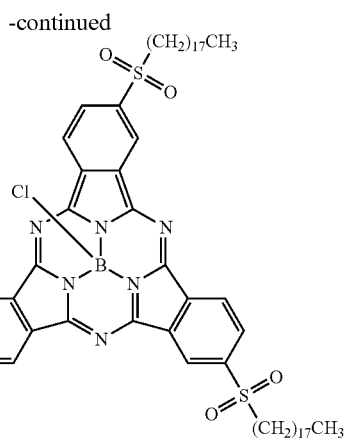

To a 500 mL three-necked, round-bottom flask equipped with Dean-Stark trap, condenser, and TEFLON coated stir magnet was charged 8.75 g of the Intermediate from Example 6A and 200 mL xylenes. The flask was placed in a 160° C. oil bath under magnetic stirring, condenser, Dean-Stark apparatus and light nitrogen blanket. After refluxing for 5 hours to remove all water, 20 mL of 1.0M boron trichloride in xylenes were added under dry conditions via syringe and septum. The solution turned a violet color and refluxing was continued. The structure was believed to be that shown above.

Example 6C

One hour after the addition of $BCl_3$ in Example 6B, the solution was quenched into a 1 L jar containing 700 mL methanol. The sample was allowed to settle for 2 days, after which the solvent was decanted off. A deep magenta oil was left. A strong magenta color was apparent in toluene solution. The structure was believe to be:

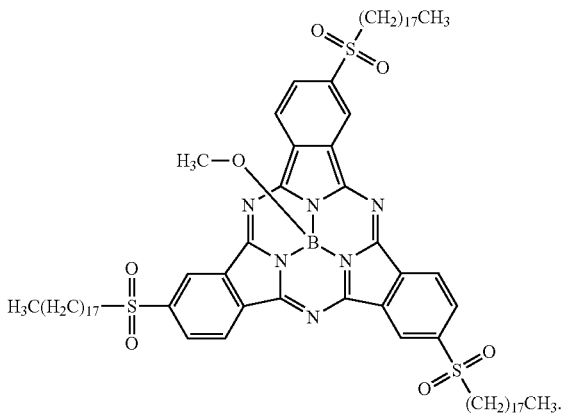

Example 7

Preparation of Ink Carrier

An ink carrier was prepared by melting, mixing, and filtering the following ingredients:
  polyethylene wax (PE655, Baker Petrolite, Tulsa, Okla., $CH_3(CH_2)_{50}CH_3$), 43.59 parts by weight;
  stearyl stearamide wax (KEMAMIDE® S-180, Crompton Corporation, Greenwich, Conn.), 19.08 parts by weight;
  tetraamide resin obtained from the reaction of one equivalent C-36 dimer acid (Uniqema, New Castle, Del.) with two equivalents of ethylene diamine and UNICID® 700 (Baker Petrolite, Tulsa, Okla., a long chain hydrocarbon having a terminal carboxylic acid group) (prepared as described in Example 1 of U.S. Pat. No. 6,174,937), 18.94 parts by weight;
  urethane resin obtained from the reaction of two equivalents ABITOL E hydroabietyl alcohol (Hercules Inc., Wilmington, Del.) and one equivalent isophorone diisocyanate (prepared as described in Example 1 of U.S. Pat. No. 5,782,966), 11.71 parts by weight;
  urethane resin that is the adduct of three equivalents stearyl isocyanate and a glycerol-based alcohol (prepared as described in Example 4 of U.S. Pat. No. 6,309,453), 6.48 parts by weight; and
  NAUGUARD® 445 antioxidant (Uniroyal Chemical Co., Middlebury, Conn.), 0.20 parts by weight.

600 g of the ink carrier components were added to a 1 L beaker and heated in an oven at 135° C. until molten. Subsequently, the beaker was inserted into a heating mantle set to 135° C. and the contents of the beaker were stirred for 45 min. The resulting ink was then filtered through a combination of Whatman #3 and 0.2 μm NAE filters and placed in a Mott filter assembly. The ink carrier was poured into molds containing about 31 g of the colorless carrier and allowed to cool.

Example 8

Ink Preparation

About 30.7 g of ink carrier from Example 7 were placed in a 100 mL beaker with a magnetic stir bar and subsequently placed in a 135° C. oil bath until molten. About 0.45 g of the m-pentadecylphenol substituted subphthalocyanine trifluoromethane sulfonic ester prepared as described in Example 4A was then added and stirred for about 3 hours. The magenta colored ink was then poured into an aluminum mold.

Example 9

Ink Preparation

About 30.9 g of ink carrier prepared as described in Example 7 were placed in a 100 mL beaker with a magnetic stir bar and subsequently placed in a 135° C. oil bath until molten. About 0.57 g of the m-pentadecylphenol substituted subphthalocyanine methane sulfonic ester prepared as described in Example 4B was then added and stirred for 3 hours. The magenta colored ink was then poured into an aluminum mold.

Example 10

Ink Preparation

About 30.4 g of ink carrier prepared as described in Example 7 were placed in a 100 mL beaker with a magnetic stir bar and subsequently placed in a 135° C. oil bath until molten. About 0.51 g of the m-pentadecylphenol substituted subphthalocyanine dodecylbenzene sulfonic ester prepared as described in Example 4C was then added and stirred for 3 hours. The magenta colored ink was then poured into an aluminum mold.

Example 11

Ink Preparation

About 30.6 g of ink carrier prepared as described in Example 7 were placed in a 100 mL beaker with a magnetic stir bar and subsequently placed in a 135° C. oil bath until molten. About 0.51 g of the m-pentadecylphenol substituted subphthalocyanine trifluoroacetate ester prepared as described in Example 3 was then added and stirred for 3 hours. The magenta colored ink was then poured into an aluminum mold.

Example 12

Fingerprint and Tape Diffusion Measurements

A test ink was prepared containing the m-pentadecylphenol substituted subphthalocyanine isopropyl ether colorant prepared as described in Example 2 and the ink carrier prepared as described in Example 7. K-proofer print samples were prepared from the ink on paper and a "fingerprint" test was carried out as follows. Shortly after print preparation, a test person sparingly spread a hand lotion on the fingers, and brought the fingertips with light to moderate pressure into contact with the print surface. The exposed samples were then stored for 5 days at room temperature, after which period they were inspected. A moderate to weak enhancement of exposed parts of the print surface was noted, particularly in the region with high ink coverage.

Dyes that are not very soluble will "bloom" or aggregate and the above "fingerprint" test expedites those two processes. The results as described above show acceptable solubility of the m-pentadecylphenol substituted subphthalocyanine isopropyl ether dye in the wax-based ink.

Two additional K-proofer print samples were prepared. Shortly after print preparation, transparent adhesive tape was affixed on parts of the edges between printed and non-printed regions of the page. One sample was then exposed to 60° C., the other remained at ambient temperature. After five days, both samples were inspected for development of diffuse edges between printed and non-printed regions. It was found that the sample which was exposed to the higher temperature showed a moderately diffuse edge, whereas the room temperature sample kept a sharp edge, indicating sufficient resistance against tape adhesive-induced dye migration.

Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all sub-ranges subsumed therein.

While the present teachings have been illustrated with respect to one or more implementations, alterations and/or modifications can be made to the illustrated examples without departing from the spirit and scope of the appended claims. In addition, while a particular feature of the present teachings may have been disclosed with respect to only one of several implementations, such feature may be combined with one or more other features of the other implementations as may be desired and advantageous for any given or particular function. Furthermore, to the extent that the terms "including," "includes," "having," "has," "with," or variants thereof are used in either the detailed description and the claims, such terms are intended to be inclusive in a manner similar to the term "comprising." Further, in the discussion and claims herein, the term "about" indicates that the value listed may be somewhat altered, as long as the alteration does not result in nonconformance of the process or structure to the illustrated embodiment. Finally, "exemplary" indicates the description is used as an example, rather than implying that it is an ideal.

It will be appreciated that variants of the above-disclosed and other features and functions, or alternatives thereof, may be combined into many other different systems or applications. Various presently unforeseen or unanticipated alternatives, modifications, variations, or improvements therein may be subsequently made by those skilled in the art which are also intended to be encompasses by the following claims.

What is claimed is:

1. A process for making a colorant compound, the process comprising:
    reacting a phthalonitrile compound with a boron halide salt to form a boron subphthalocyanine chloride intermediate, the phthalonitrile compound including an oxygen or sulfur containing functional group substituted with a substituted or unsubstituted, linear, branched or cyclic, aliphatic or aromatic terminal hydrocarbyl group that is 8 or more carbon atoms in length, the hydrocarbyl group optionally containing one or more heteroatoms; and
    reacting the boron subphthalocyanine chloride intermediate with at least one oxygen containing compound selected from the group consisting of carboxylic acids and sulfonic acids to form a colorant compound that provides a magenta color,
    wherein the carboxylic acid has a formula:

$R_5COOH$ wherein $R_5$ is a substituted or unsubstituted alkyl optionally containing one or more hetero atoms; and the sulfonic acid has a formula:

$R_6S(=O)_2OH$ wherein $R_6$ is a substituted or unsubstituted alkyl optionall containing one or more hetero atoms.

2. The process of claim 1, wherein the phthalonitrile compound is selected from the group consisting of a $C_{10}$ to $C_{50}$ alkyl phenoxy substituted phthalonitrile or a $C_{10}$ to $C_{50}$ alkyl sulfone substituted phthalonitrile.

3. The process of claim 1, wherein the boron halide salt is boron trichloride.

4. The process of claim 1, wherein the oxygen containing compound is the carboxylic acid.

5. The process of claim 1, wherein the oxygen containing compound is the sulfonic acid.

6. The process of claim 1, wherein the phthalonitrile compound is made by mixing an alkylsulfide-phthalonitrile, an oxidizer and a solvent to form an alkyl sulfone substituted phthalonitrile.

* * * * *